United States Patent [19]

De Stasio

[11] 4,365,784
[45] Dec. 28, 1982

[54] APPARATUS FOR OBTAINING A TEST CORE

[76] Inventor: Joseph R. De Stasio, 710 Shore Rd., Spring Lake Heights, N.J. 07762

[21] Appl. No.: 233,293

[22] Filed: Feb. 10, 1981

[51] Int. Cl.³ .............................. B28B 7/10; B29C 1/16
[52] U.S. Cl. ................................... 249/139; 73/864.53; 73/864.59; 249/177; 249/184; 249/205; 249/DIG. 4; 264/31
[58] Field of Search ................. 249/DIG. 4, 139, 156, 249/157, 177, 184, 205; 264/31; 73/864.51, 864.53, 864.59

[56] References Cited

U.S. PATENT DOCUMENTS

| | | | |
|---|---|---|---|
| 1,603,748 | 10/1926 | Davis | 249/157 |
| 1,963,362 | 6/1934 | Gooder | 264/31 |
| 2,891,466 | 6/1959 | Foster | 249/157 |
| 2,986,797 | 6/1961 | Aisenberg | 249/DIG. 4 |
| 3,163,908 | 1/1965 | Lawmaster | 249/DIG. 4 |
| 3,176,053 | 3/1965 | Di Stasio | 249/DIG. 4 |

Primary Examiner—James B. Lowe
Attorney, Agent, or Firm—James & Franklin

[57] ABSTRACT

During positioning of the cylindrical, open ended, outer member relative to a point on a slab form, a cap member may be used to cover the top and support a location determining member. The length of the outer member is adjustable to the thickness of the concrete layer to be poured. A cylindrical inner member, with a closed bottom and an open top, is inserted into the outer member. As the concrete is poured, it is received in the inner member and forms the test core. After the concrete sets, the inner member is removed, resulting in a hole in the concrete. The cap member is alternatively adapted to close the bottom of the outer member, prior to mounting the outer member on the form, to permit the hole to be subsequently filled, if the form has been removed.

20 Claims, 3 Drawing Figures

APPARATUS FOR OBTAINING A TEST CORE

The present invention relates to apparatus for obtaining a test core from a concrete layer, poured on a slab form or the like and, more particularly, to a cap member which can be used either to close the bottom of the outer member of the apparatus to permit filling of the hole resulting from the removal of the test core, if the slab form has been previously removed, or which can be used on top of the outer member as a support for a location determining member, to facilitate accurate positioning of the axis of the member, and to a novel structure of the outer member which permits the effective length of the outer member to be adjusted to accommodate different thicknesses of concrete.

Many structural elements, such as roadways and floors of buildings, are formed of plastic materials, such as concrete and the like, which are permitted to set in place. The only positive manner of determining the nature and, particularly, the strength of the set material is to take a sample of the layer. Because of the difficulties, expense and time involved in removing a sample from a hard concrete mass or the like, the conventional procedure was to pour a test cylinder separate from the floor and to take actual hardened core samples from the floor only when the test cylinders indicate a possible problem. When required, the removal of a test core from the hardened floor itself may be accomplished by drilling with a diamond tool. However, this entails considerable labor, water, the presence of compressed air lines and a specialized tool. Moreover, in removing the test core, it was necessary to avoid cutting the reinforcements within the concrete which would destroy the carrying capacity of the structural slab element. Thus, removal of the test core in this fashion is to be avoided, if possible.

My U.S. Pat. No. 3,176,053, granted Mar. 30, 1965 and entitled: "Method For Obtaining Test Cores", relates to an apparatus which permits one to obtain a test core directly from the concrete layer at minimal expanse. As set forth in detail in that patent, the apparatus comprises a two-piece core forming structure including an outer member and an inner member which is freely telescopically received within and removable from the outer member. The outer member is mounted on the slab form where the concrete layer is to be formed. The inner member is telescoped therein, with air space between inner and outer members. A flange is provided on the inner member which fixes the depth to which the inner member is received into the outer member. The outer member is provided with an open top for receiving the inner member.

The concrete layer is then poured and enters the inner member which is also provided with an open top. After the concrete has hardened, the inner member is simply lifted, by prying under the flange, and extracted from the outer member. The concrete core is removed from the inner member, either by splitting the the inner member and peeling same away, or by pushing the core from the inner member by means of an aperture in the bottom of the inner member provided for this purpose. The core may then be subjected to the desired laboratory testing.

While the above-described method and apparatus has worked well over the years, I have found that there are several desirable functions which the apparatus described above cannot perform. First, the open bottom of the outer member prevents the filling of the hole, resulting from test core removal, once the slab form has been removed. Second, the outer member is difficult to accurately locate on the form, although same is required if the hole resulting from removal of the test core is to be used for vertical conduit, wires, cable, etc. Third, the effective length of the outer member cannot be adjusted in accordance with the thickness of the layer to be poured.

As described in the above-mentioned patent, the outer member has a substantially cylindrical configuration which is open at both ends. A flange, or similar means, is provided at the bottom end for fastening to the slab form. The inner member is also cylindrical, but has a closed bottom with an open, flanged top. The inner member is telescopically received in the outer member with the flange on the top of the inner member resting on the rim of the outer member. After the concrete layer is poured on the slab form, it is permitted to set. The inner member, with the test core therein, is removed, resulting in a cylindrical opening in the concrete.

In certain instances, it is necessary to fill the hole with a concrete plug. However, the concrete form may have been removed before a concrete plug could be installed to fill the hole. Once the form is removed, a concrete plug can no longer be poured into the hole because of the open bottom of the outer member. Thus, if the hole required filling, a new form part had to be installed, below the layer, to act as a base to hold the new concrete plug. The installation of the new form part is, however, impractical because it is difficult, expensive and cumbersome to construct.

It is also necessary, when the hole is filled, that the concrete plug be anchored securely to the inner wall of the outer member and that the outer member be anchored securely to the surrounding slab. If it were not so, a downward force on the top of the plug could cause the plug to dislodge from the layer and fall to the floor below, creating a potential hazard.

On the other hand, it is often useful to have a hole through the concrete layer, to permit the running of vertical conduits, cables, wires, or the like, therethrough. When this is the case, it is necessary to very accurately position the axis of the apparatus at a precisely determined location on the slab, such that after the concrete is poured and the test core removed, the resulting hole will be in the required location for the conduit.

Since concrete layers or slabs are formed with varying thicknesses, and the length of the outer member of the test core apparatus must be equal to the thickness of the layer, it was necessary to provide a variety of different length outer members to accommodate concrete layers of different thicknesses. This results in increased inventory and manufacturing costs.

It is, therefore, a prime object of the present invention to provide an improved apparatus for obtaining a test core which includes a cap member capable of sealing the open bottom of the outer member, to permit installation of a concrete plug to fill the hole resulting from removal of the test core, after the slab form has been removed.

It is another object of the present invention to provide an improved apparatus for obtaining a test core which includes a cap member which can be utilized as a support for a location determining member, to facilitate accurate positioning of the apparatus on the form, such that the resulting vertical hole can be utilized for the running of vertical conduit or the like.

It is another object of the present invention to provide improved apparatus for obtaining a test core wherein the same cap member can be alternatively used to perform either of the above-mentioned functions.

It is another object of the present invention to provide improved apparatus for obtaining a test core wherein the outer member comprises means for adjusting the effective length thereof, so as to accommodate concrete layers of a variety of different thicknesses.

It is another object of the present invention to provide apparatus for obtaining a test core having means for securely anchoring a plug, filling the hole resulting from removal of the inner member, to the concrete layer, to prevent dislodging of same.

In accordance with the present invention, apparatus is provided for obtaining a test core from a concrete layer poured on a form. The apparatus comprises an outer member, having an open bottom with a flange for fastening to the form, and an open top, an inner member, having a closed bottom and open top, adapted to be inserted within the outer member to receive concrete therein, and a cap member. The cap member comprises means thereon, alternatively adapted to engage and close the bottom of the outer member and to cover the top of the outer member, so as to provide a support for a location determining member.

The outer member comprises first and second parts and means for adjustably positioning said parts relative to each other to adjust the effective length of the outer member. The adjusting means comprises intermeshing screw threads.

The cap member has a circular end and the means comprises a substantially cylindrical wall extending from the end. The wall comprises external means for removably engaging the interior of the first part and an internal surface for engaging the top of the second part.

A location determining means, in the form of a rod, is provided, as is a recess on the cap surface, adapted to receive the end thereof. The recess is located at the axis of rotation of the cap member.

Means are provided on the inner wall of the outer member to securely anchor a concrete plug thereto. Similarly, means are provided on the outer wall of the outer member to securely anchor the outer member to the surrounding concrete layer. These means prevent a concrete plug, installed after the removal of the test core, to fill the hole, from being dislodged from the concrete layer or slab.

To these objects and to those which may hereinafter appear, the present invention relates to an improved apparatus for obtaining a test core, as set forth in the following specification and recited in the annexed claims, taken together with the accompanying drawings, wherein like numerals refer to like parts, and in which:

Figure 1:
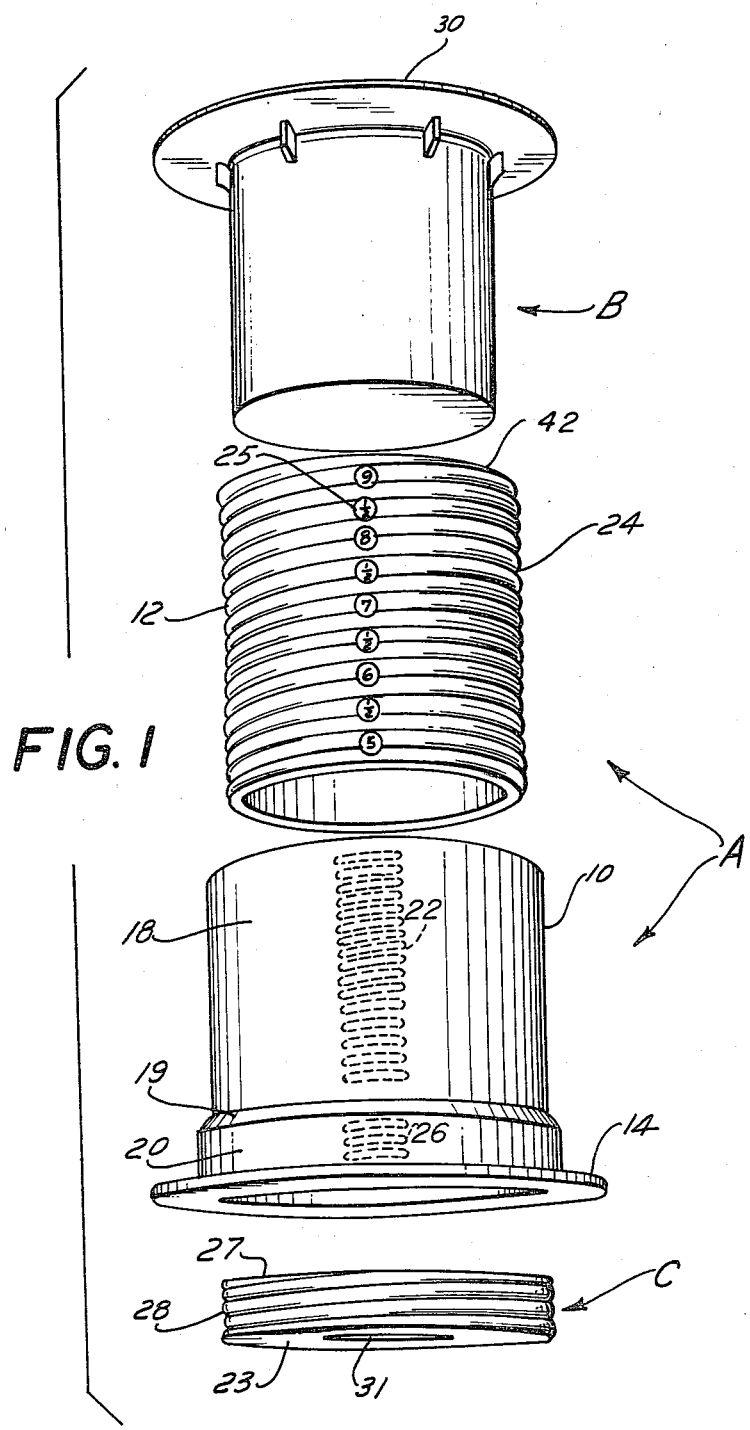
FIG. 1 is an exploded isometric view of the apparatus of the present invention.

As seen in the drawings, the apparatus of the present invention comprises an outer member, generally designated A, an inner member, generally designated B, and a cap member, generally designated C, all of which are preferably composed of a suitable plastic material. Outer member A comprises a first part 10 and a second part 12. Part 10 is generally cylindrical in nature and has an open bottom and top. A flange 14 extends outwardly from the open bottom of part 10 and is provided with a plurality of openings 16 (not shown in FIG. 1), through which nails or other suitable fastening devices may be inserted so as to affix the flange 14 and, thus, part 10 to a slab form or the like, upon which a concrete layer will be poured.

The body portion of part 10 comprises two sections 18 and 20 with a ridge or shoulder 19 therebetween. Section 18, forming the upper portion of part 10, has an inner diameter slightly greater than the outer diameter of part 12 and is provided with internal screw threads 22, adapted to meshingly engage the external screw threads 24 on part 12. Thus, the rotation of part 12 with respect to part 10 changes the effective overall length of outer member A such that same can accommodate concrete layers of different thicknesses. The threads 24 are preferably calibrated by numbers 25 to facilitate adjustment to the desired setting, based upon height of layer, in inches.

The lower section 20 of part 10 has a slightly larger inner and outer diameter than does section 18 and is also provided with internal screw threads 26 which are adapted to meshingly interengage the external threads 28 on cap member C. The length of part 20, that is, the distance between flange 14, at the bottom of part 10, and the bottom of section 18 thereof is approximately equal to the height of cap member C, such that cap member C can be completely received within section 20.

Part 12 has a substantially cylindrical configuration with a smooth inner surface and screw threads 24 on the exterior surface thereof which, as mentioned above, are adapted to meshingly engage with screw threads 22 on the interior of section 18 of part 10. Part 12 has an open bottom and an open top.

The exposed threads 22 (those not meshing with threads 24) on the inner wall of part 10 and the interior of shoulder 19 form "keys" for anchoring a concrete plug to the outer member, when same is installed within the outer member to fill same, after removal of the test core. Similarly, the exposed threads 24 (those not meshing with threads 22) on the exterior of part 12 and the exterior of shoulder 19 form "keys" for securely anchoring the outer member to the surrounding concrete layer or slab. Thus, a concrete plug, installed to fill the hole remaining after removal of the test core is prevented from being dislodged from the concrete layer or slab.

Inner member B is also substantially cylindrical and has an outer diameter slightly smaller than the inner diameter of part 12, such that member B can be telescopically received within part 12. The upper rim of member B is provided with a flange 30 which rests on the top rim 42 of part 12, when member B is received within member A. Flange 30 also acts as a grip to facilitate removal of member B from member A, after the concrete has been poured and set. Member B has a closed bottom to retain the test core therein.

Figure 2:
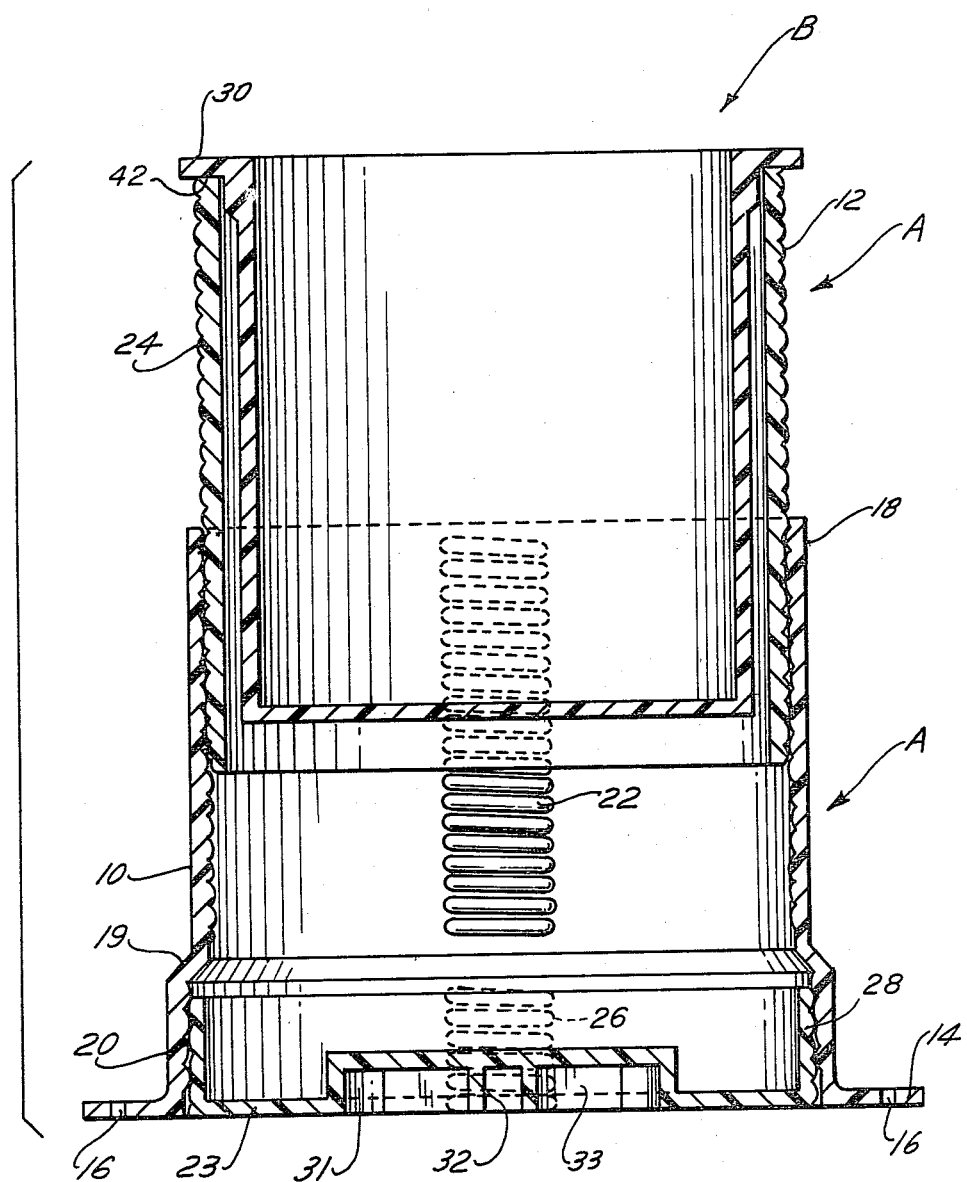
FIG. 2 is a cross-sectional view of the apparatus of the present invention, showing the cap member in position aligned to seal the open bottom of the outer member.

Cap member C has a cup-shaped structure, with a circular surface 23 and an upstanding cylindrical wall 27 having screw threads 28, the outer diameter of which is slightly less than the inner diameter of section 20 of part 10, such that it can be received therein in order to seal the bottom of member A. As shown in FIG. 2, cap member C is rotated into section 20 of part 10 such that threads 28 mesh with threads 26. A circular recess 31, provided on the surface 23 of the cap, is divided into four finger-tip receiving compartments by four upstanding walls 33 and facilitates the rotation of cap member C.

Figure 3:
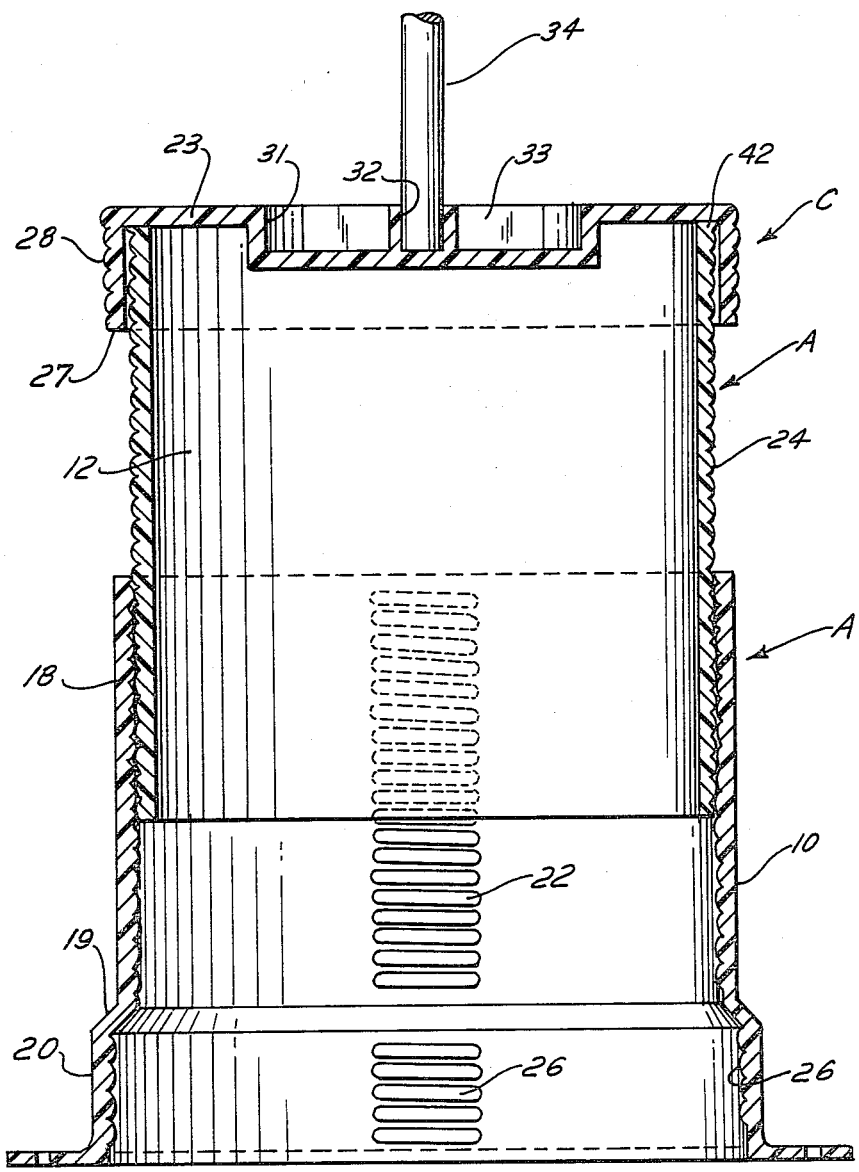
FIG. 3 is a cross-sectional view of the apparatus of the present invention with the cap member in position on top of the outer member to support a location determining member.

The inner diameter of wall 27 of member C is slightly larger than the outer diameter of part 12, such that cap member C can be received over the rim 42 of part 12, as illustrated in FIG. 3. The top surface 23 of cap member C is provided with a central recess 32, within recesses 31, along the axis of the cap member. When cap member C is received on part 12, as shown in FIG. 3, recess 32 will indicate the position of the axis of the apparatus. Recess 32 is designed to receive the end of a rod 34 therein, such that the axis of the outer member A can be accurately positioned at a predetermined location on the slab form.

In order to obtain a test core, outer member A is fastened to the slab form by inserting nails or screws through apertures 16 in flange 14, which skirts the normally open bottom of the member A. Part 12 is then rotated into section 18 of part 10 until the rim 42 thereof is at a distance from the slab form equal to the thickness of the concrete layer to be formed. Inner member B is inserted within part 12, such that flange 30 rests on rim 42 of part 12. The concrete layer is then poured on the slab form and fills the interior of member B. The concrete is permitted to set and, thereafter, member B, with the test core therein, is removed from outer member A by simply grasping flange 30 and lifting upward. The concrete test core is removed from member B by slitting the side of member B, along a vertical cut or indentation (not shown) molded in the wall of member B, by means of a knife blade or the like, and peeling member B from the test core.

After member B, with the test core therein, is removed from member A, a hole remains in the concrete which is defined by outer member A. This hole extends through the entire concrete layer and, once the form is removed, may be used to run vertical conduit, cable, wires or the like through the layer. Otherwise, the hole must be filled. If the hole is to be used, such as to run conduit or the like, the axis of the hole must be accurately positioned within the concrete slab. The accurate positioning of the hole requires that the outer member A be accurately positioned on the slab form when it is mounted thereto. This may be accomplished, prior to permanently affixing the outer member to the slab form, by using cap member C, in the manner shown in FIG. 3.

In this instance, cap member C is received over the rim 42 of part 12 of member A. The inner diameter of cap member C is slightly larger than the outer diameter of part 12 to permit member C to be situated thereon. A rod 34 is then received within recess 32 on the surface of cap C. Rod 34 defines the axis or center line of the hole which will result when the member B is removed from the apparatus. Thus, the distance between rod 34 and some fixed point of reference on the slab form is determined such that the center line of the hole will be in precisely the required position.

On the other hand, in some instances, the hole cannot be used and must be filled. If the hole had been filled before the slab form was removed, concrete could have simply been poured into the hole and permitted to set, because the form would act as a base for the concrete. However, once the slab form has been removed, no base exists for the concrete to be poured into member A and the hole could not normally have been filled.

However, cap member C is designed to be received in the bottom of outer member A, in section 20 thereof, prior to mounting the outer member to the form. In this manner, cap member C may be used to close the bottom of outer member A and, therefore, provide a base for the newly poured concrete used to plug the hole.

Thus, the structure of cap member C permits it to provide alternate functions. The cap can be used to close the bottom of outer member A, such that the hole resulting from the removal of the test core can be filled with concrete, after the slab form has been removed. Alternatively, cap member C can be situated on the rim of part 12 of member A and used in conjunction with a rod 34 to accurately position the apparatus and, thus, the hole which will result from the removal of the test core from the apparatus.

The outer member is designed to provide means, on the interior wall thereof, to securely anchor a concrete plug thereto, and means, on the exterior wall thereof, to securely anchor the outer member to the surrounding concrete layer or slab. These means prevent the dislodgment of the concrete plug from the layer or slab.

In addition, the two-part structure of outer member A permits the adjustment of the effective length of member A simply by rotating part 12 with respect to part 10. In this manner, a single outer member can be used with concrete layers of varying thicknesses.

While only a single preferred embodiment of the present invention is disclosed herein for purposes of illustration, it is obvious that many variations and modifications could be made thereto. It is intended to cover all of these variations and modifications which fall within the scope of the present invention, as defined by the following claims:

I claim:

1. Apparatus for obtaining a test core from a concrete layer poured on a form comprising an outer member, having an open bottom and top, an inner member, having a closed bottom and open top, and being adapted to be inserted within said outer member so as to receive concrete therein, and a cap member, having means thereon alternatively adapted to engage and close said bottom of said outer member, and to cover said top of said outer member, so as to provide a support for a location determining member.

2. The apparatus of claim 1, wherein said outer member comprises first and second parts and means for adjustably positioning said parts relative to each other to adjust the effective length of said outer member.

3. The apparatus of claim 2, wherein said position adjusting means comprises internal screw threads on said first part and external screw threads on said second part.

4. The apparatus of claim 1, wherein said cap member has a substantially circular end and wherein said means comprises a substantially cylindrical wall extending from said end.

5. The apparatus of claim 4, wherein said wall comprises external surface for removably engaging the interior of said first part.

6. The apparatus of claim 4, wherein said wall comprises internal surface for engaging the top of said second part.

7. The apparatus of claim 5, wherein said wall comprises internal surface for engaging the top of said second part.

8. The apparatus of claim 2, wherein said first part comprises a cap receiving section and a second part receiving section, said cap receiving section having a larger inner diameter than said second part receiving section.

9. The apparatus of claim 8, wherein said cap member has an inner diameter larger than the outer diameter of said second part.

10. The apparatus of claim 8, wherein said cap member has an outer diameter smaller than the inner diameter of said cap receiving section.

11. The apparatus of claim 1, further comprising location determining means and means on said cap member for mounting said location determining means.

12. The apparatus of claim 11, wherein said location determining means comprises a rod and wherein said mounting means comprises a recess in said cap member, adapted to receive one end of said rod.

13. The apparatus of claim 12, wherein said recess is aligned with the axis of rotation of said cap member.

14. The apparatus of claim 1, further comprising means, on the interior wall of said outer member, for securely anchoring a concrete plug thereto.

15. The apparatus of claim 1, further comprising means, on the exterior wall of said outer member, for securely anchoring same to the concrete layer.

16. Apparatus for obtaining a test core from a concrete layer poured on a form comprising: an outer member, comprising a first part, having means for securing same to the form, a second part having a rim and means for adjustably positioning said second part relative to said first part; and an inner member adapted to be inserted within said outer member and having a flange at the top thereof adapted to rest on said rim, said inner member having an open top to receive concrete therein.

17. The apparatus of claim 16, wherein said first part comprises a cap receiving section and a second part receiving section, said cap receiving section having a larger inner diameter than said second part receiving section.

18. The apparatus of claim 16, wherein said position adjusting means comprises internal screw threads on said first part and external screw threads on said second part.

19. The apparatus of claim 16, further comprising means, on the interior wall of said outer member, for securely anchoring a concrete plug thereto.

20. The apparatus of claim 16, further comprising means, on the exterior wall of said outer member, for securely anchoring same to the concrete layer.

* * * * *

UNITED STATES PATENT AND TRADEMARK OFFICE
CERTIFICATE OF CORRECTION

PATENT NO. : 4,365,784

DATED : December 28, 1982

INVENTOR(S) : Joseph R. Di Stasio

It is certified that error appears in the above-identified patent and that said Letters Patent is hereby corrected as shown below:

On the title page Item [19], "De Stasio" should read -- Di Stasio --. Item [76], "Joseph R. De Stasio" should read -- Joseph R. Di Stasio --.

Signed and Sealed this

Twenty-ninth Day of March 1983

[SEAL]

Attest:

GERALD J. MOSSINGHOFF

Attesting Officer

Commissioner of Patents and Trademarks